United States Patent
Jones et al.

(10) Patent No.: US 6,607,529 B1
(45) Date of Patent: *Aug. 19, 2003

(54) ELECTROSURGICAL DEVICE

(75) Inventors: Christopher Scott Jones, Palo Alto, CA (US); Phillip R. Sommer, Newark, CA (US); James Allen Baker, Jr., Palo Alto, CA (US)

(73) Assignee: Medtronic Vidamed, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/492,272

(22) Filed: Jun. 19, 1995

(51) Int. Cl.$^7$ ............................................. A61B 18/18
(52) U.S. Cl. ............................ 606/47; 606/40; 606/46; 606/49; 607/99; 607/101; 607/115; 607/116
(58) Field of Search ................ 606/33–52; 607/99–105, 607/115, 116

(56) References Cited

U.S. PATENT DOCUMENTS

| | | |
|---|---|---|
| 2,008,526 A | 7/1935 | Wappler et al. |
| 2,038,393 A | 4/1936 | Wappler |
| 4,016,886 A | 4/1977 | Doss et al. |
| 4,474,174 A | 10/1984 | Petruzzi |
| 4,524,770 A | 6/1985 | Orandi |
| 5,342,357 A | 8/1994 | Nardella |
| 5,360,428 A | 11/1994 | Hutchinson, Jr. |
| 5,366,490 A | 11/1994 | Edwards |
| 5,370,675 A * | 12/1994 | Edwards et al. ............ 607/101 |
| 5,385,544 A | 1/1995 | Edwards |
| 5,409,453 A | 4/1995 | Lundquist |
| 5,421,819 A | 6/1995 | Edwards |
| 5,423,804 A * | 6/1995 | Kulick ........................ 606/15 |
| 5,435,805 A | 7/1995 | Edwards |
| 5,667,488 A * | 9/1997 | Lundquist et al. ............ 604/22 |

FOREIGN PATENT DOCUMENTS

WO    WO93/15664    8/1993

OTHER PUBLICATIONS

Greenwald Surgical Company, Inc., "Orandi Resectoscope Injection Needle for Injection of Local Anesthetics," (Undated) Sheet No. P000121.

E.F. Nation, M.D., "Evolution of Knife–Punch Resectoscope," (Apr. 1976) Urology, vol. VII, No. 4, pp. 417–427.

(List continued on next page.)

Primary Examiner—David M. Shay
(74) Attorney, Agent, or Firm—Thomas F. Woods

(57) ABSTRACT

An electrosurgical device comprising an elongate probe member having proximal and distal extremities and a passage extending from the proximal extremity to an opening at the distal extremity. The elongate probe member is provided with an elongate cutout adjacent the opening so that the elongate probe member is formed with an elongate extension projecting alongside the cutout beyond the opening. A guide canula is mounted in the passage of the elongate probe member and has proximal and distal extremities and a lumen extending therethrough. A radio frequency electrode is disposed in the lumen and an insulating sleeve is coaxially disposed on the radio frequency electrode. A handle is secured to the proximal extremity of the guide canula for advancing and retracting the radio frequency electrode and the insulating sleeve with respect to the guide canula and for causing bending of the distal extremity of the guide cannula into the cutout. The extension of the elongate probe member provides support to the guide cannula against the force of the radio frequency electrode engaging the tissue. A method for using the device is provided.

33 Claims, 8 Drawing Sheets

OTHER PUBLICATIONS

R. Gutierrez, "Transurethral Treatment of Bladder Neck Obstructions: Endoscopic Prostatic Resection," (Apr. 1933) History of Urology, vol. II, Chapter V, pp. 137–186.

C.W. Ogden, Heat and the Prostate from Electrolysis to Microwaves: Lessons from an Historical Perspective, (Undated) Abstract, 2 sheets, p. 366.

Graversen, et al., "Transurethral incisions of the prostate under local anaesthesia in high–risk patients: a pilot study," (1987) Abstract, HealthGate Home Page, p. P000115.

Miller, et al., "Integrated cystoscope: first rigid multipurpose operating cystoscope for local anesthetic endoscopy," (1989) Abstract, HealthGate Home Page, p. P000116.

Orandi, "Urological endoscopic surgery under local anesthesia: a cost–reducing idea," (1984) Abstract, HealthGate Home Page, p. P000117.

Orandi, "Transurethral resection versus transurethral incision of the prostate," (1990) Abstract, HealthGate Home Page, p. P000118.

H. LeVeen, "Method for treating benign and malignant tumors utilizing radio frequency," (Nov. 16, 1976) Abstract, USPTO.GOV, U.S. patent No. 3,991,770, pp. P000119–P000120.

R. Auhll, "The Use of the Resectoscope in Gynecology," (Oct. 1990) Biomedical Business International, pp. 91–99.

L. Geddes, "A Short History of the Electrical Stimulation of Excitable Tissue Including Electrotherapeutic Applications," (1984) A Supplement to The Physiologist, vol. 27, No. 1, pp. P000066–P000071.

W. Moseley, M.D., "The History of Treatment of BPH Including Current Treatment Alternatives," (Undated) pp. P000187–P000190.

D. Paulson, M.D., "Diseases of the Prostate," (1989) Clinical Symposia, vol. 41, No. 2., pp. P000191–P000195.

T. Kirwin, "The Treatment of Prostatic Hypertrophy by a New 'Shrinkage' Method," (Aug. 1934) J. Urology, pp. 481–494.

\* cited by examiner

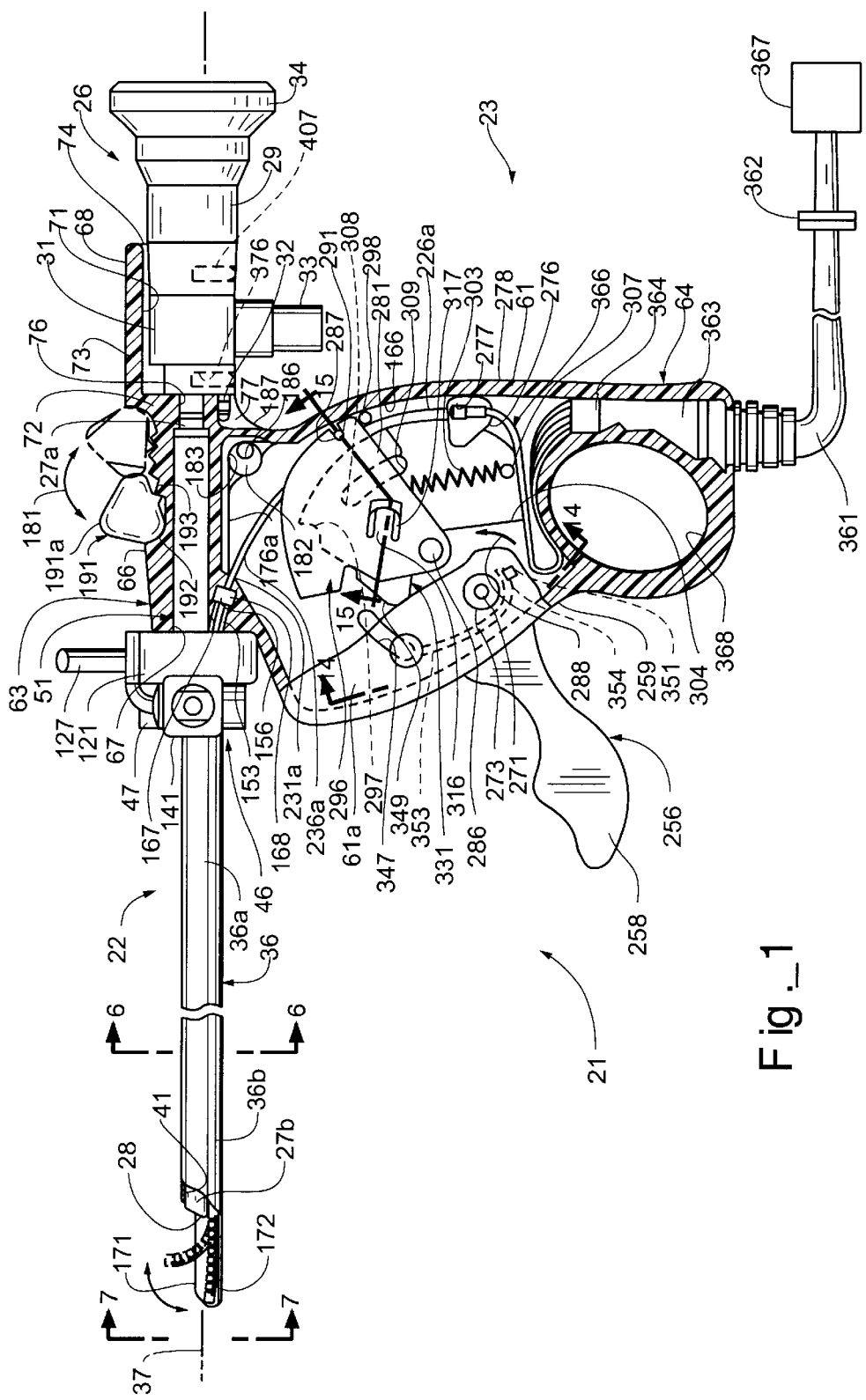
Fig._1

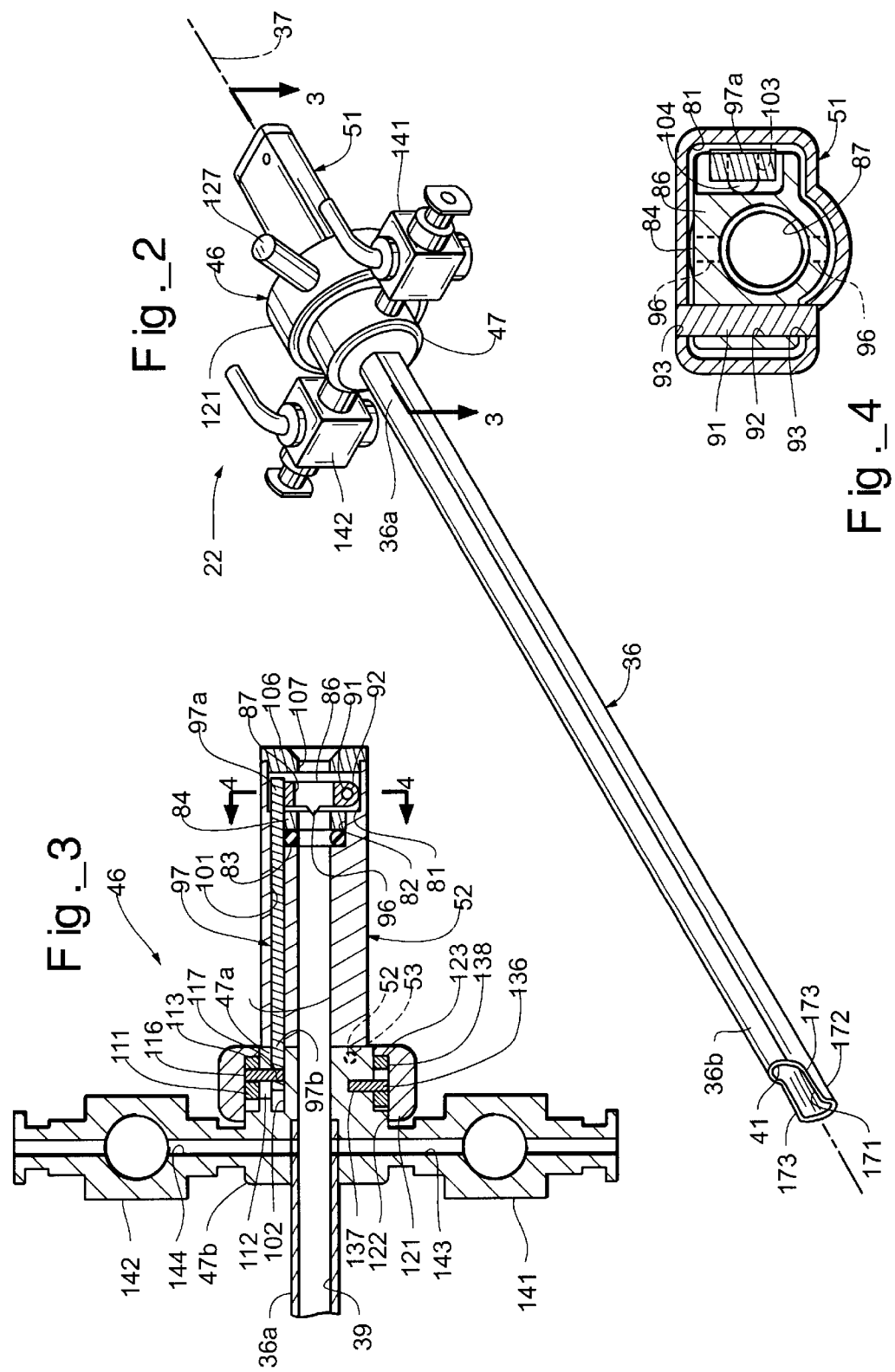

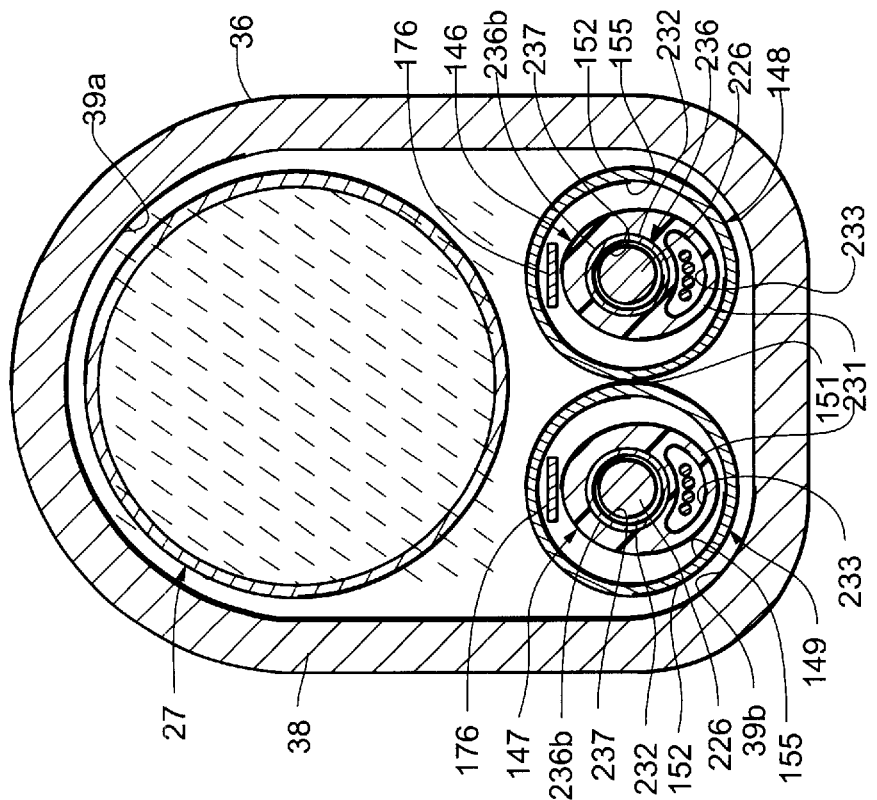
Fig._6
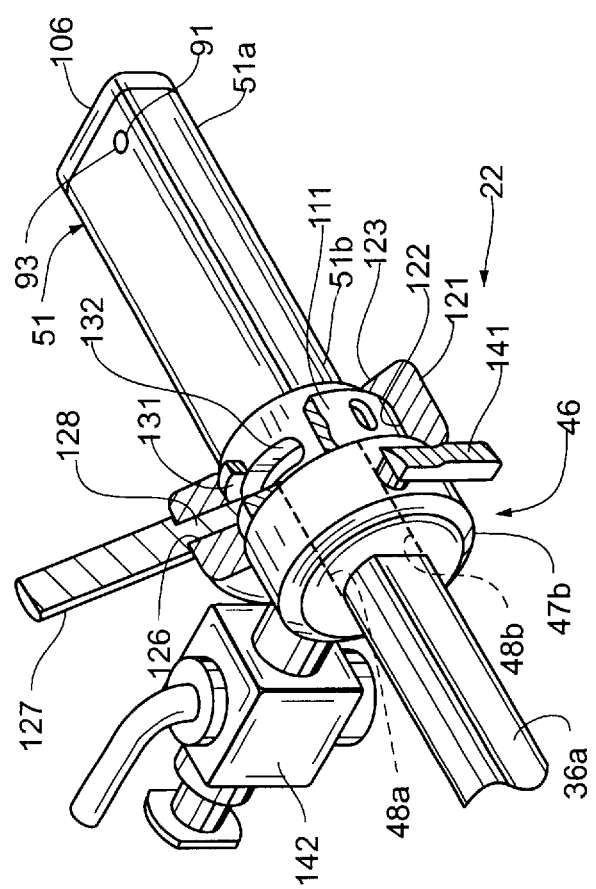
Fig._5

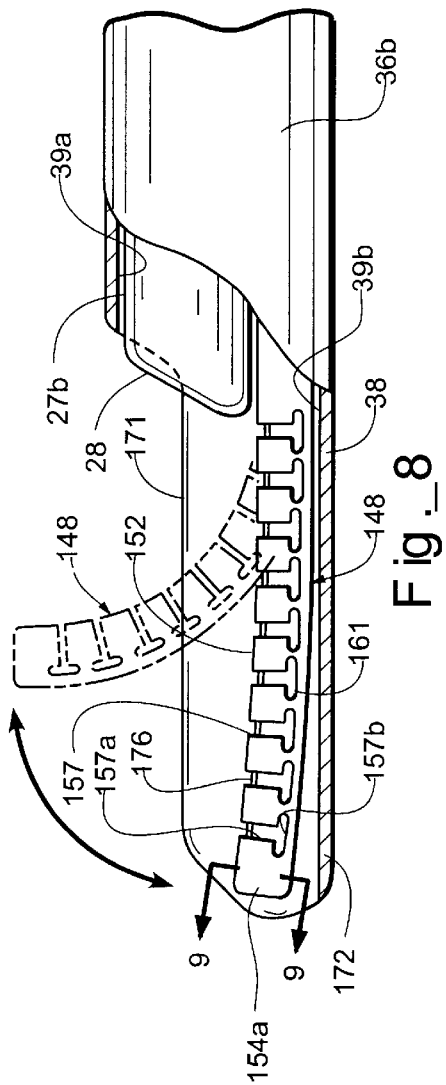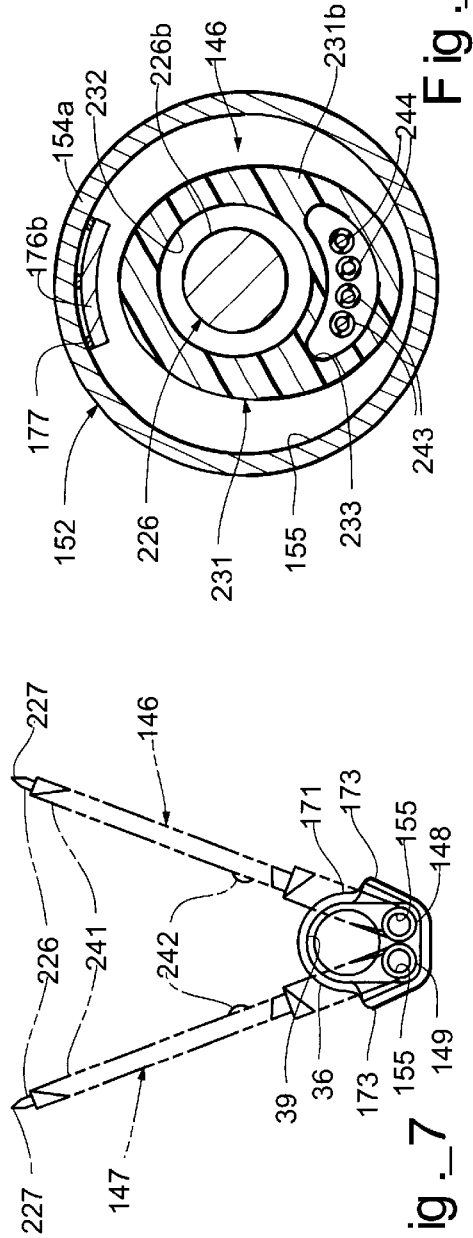

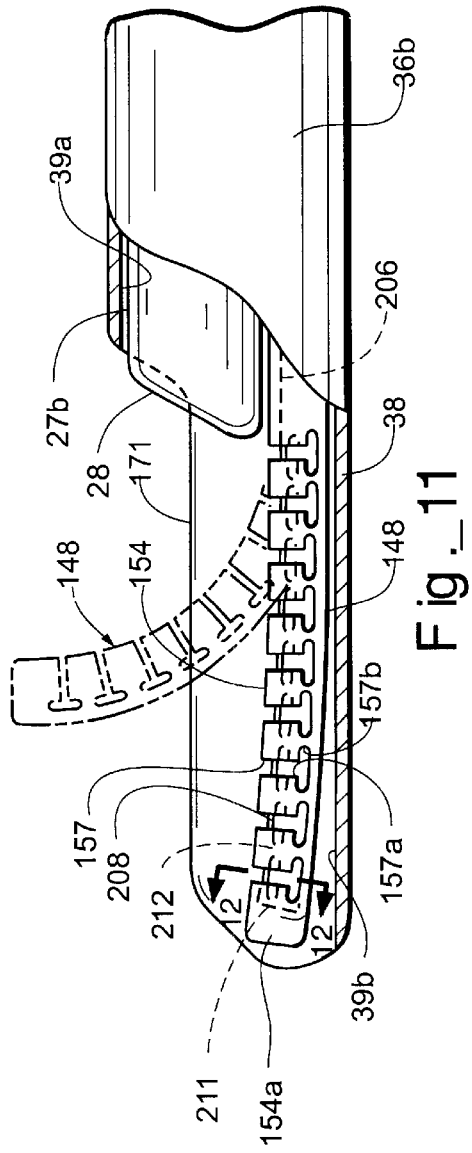
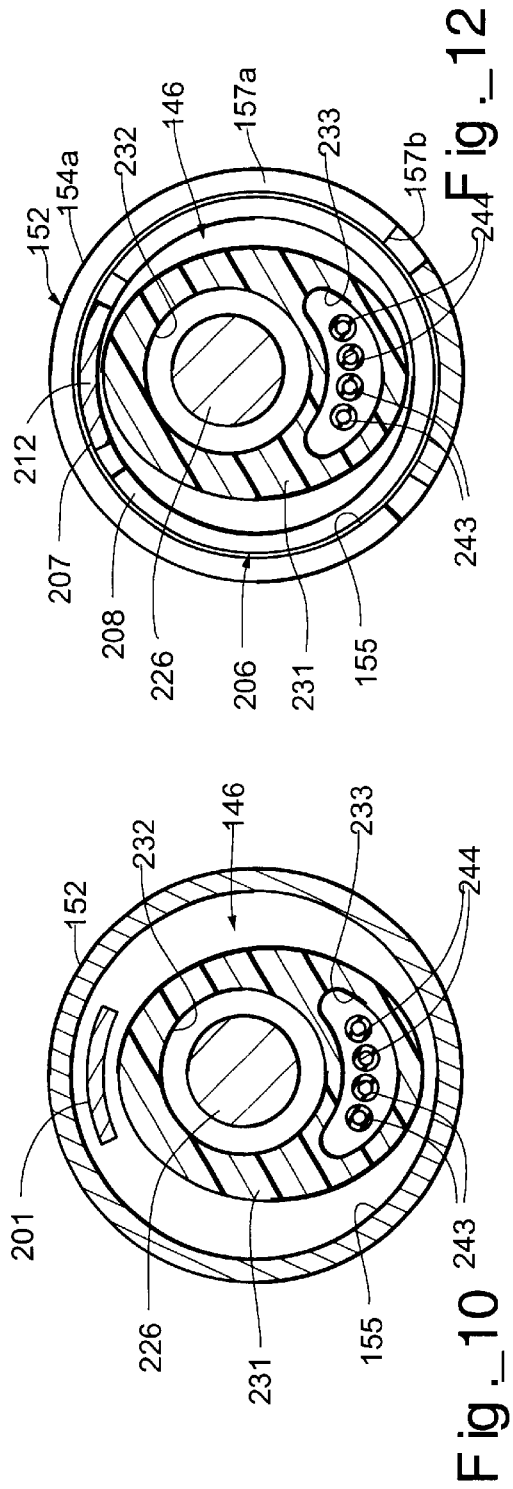

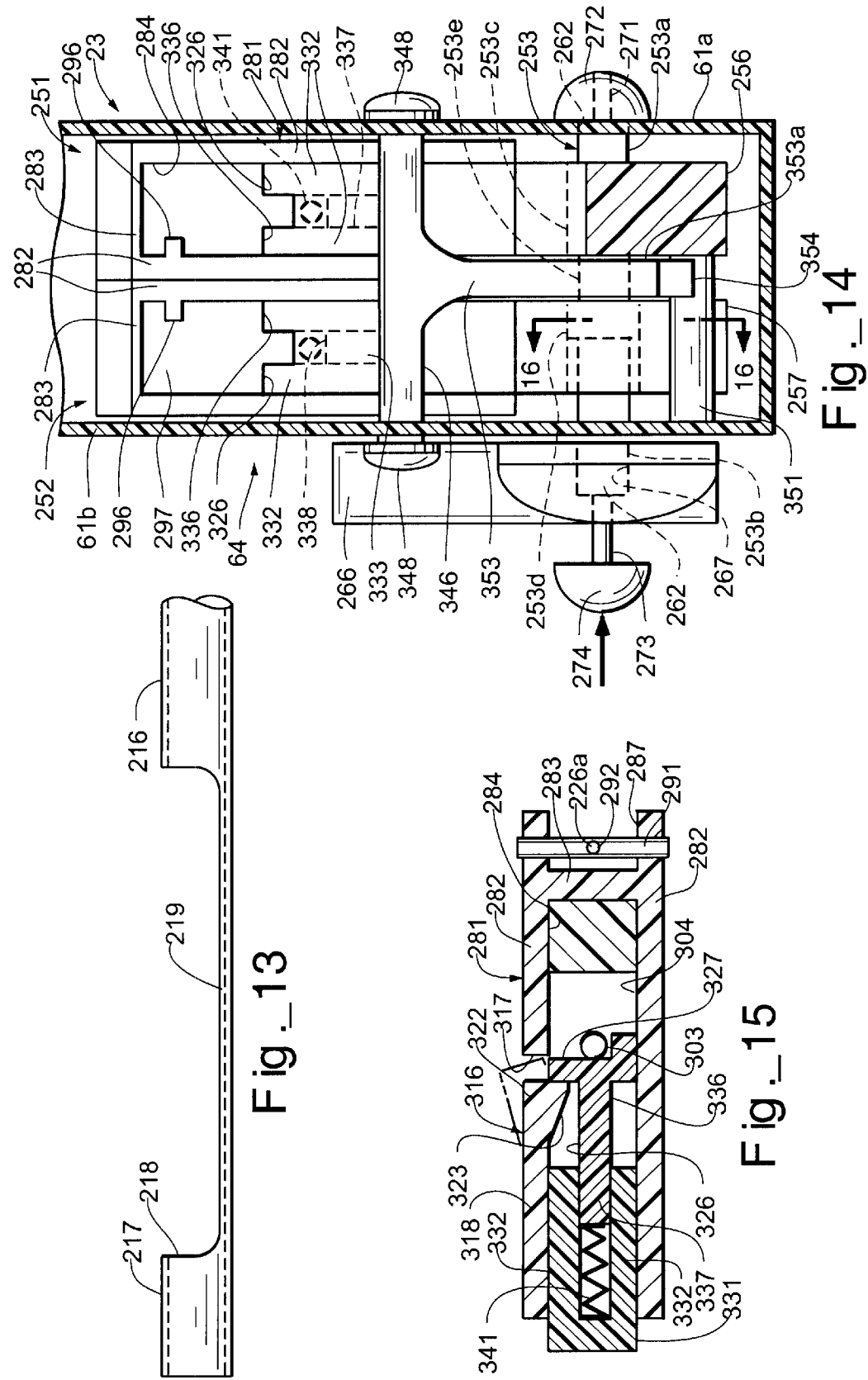

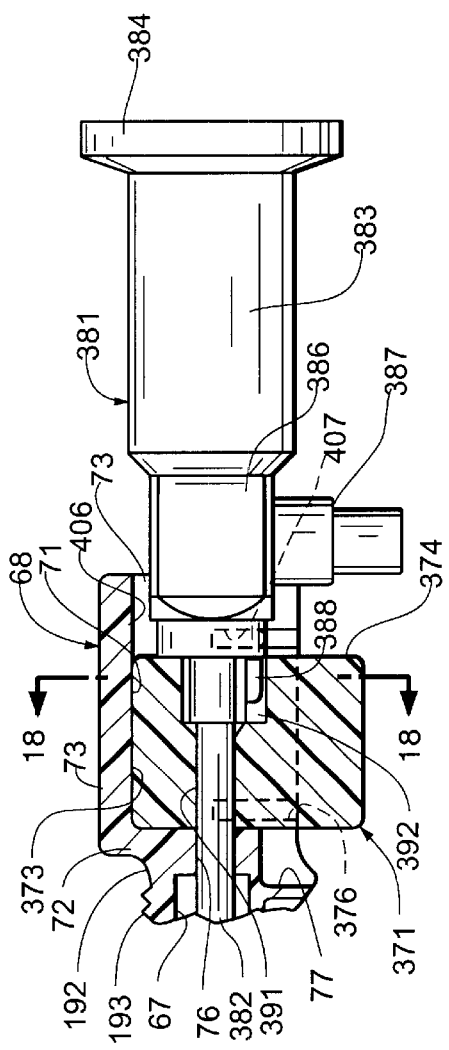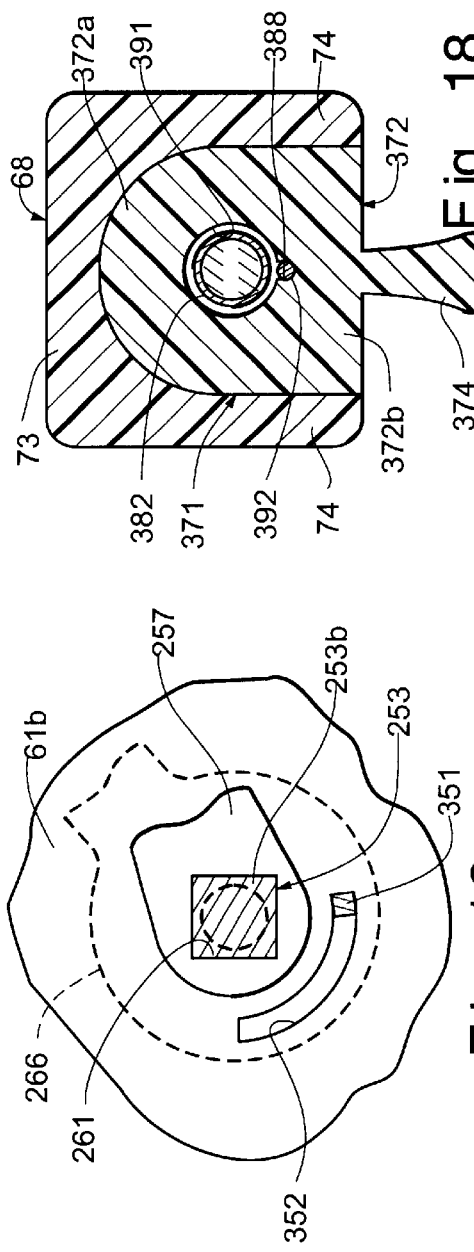

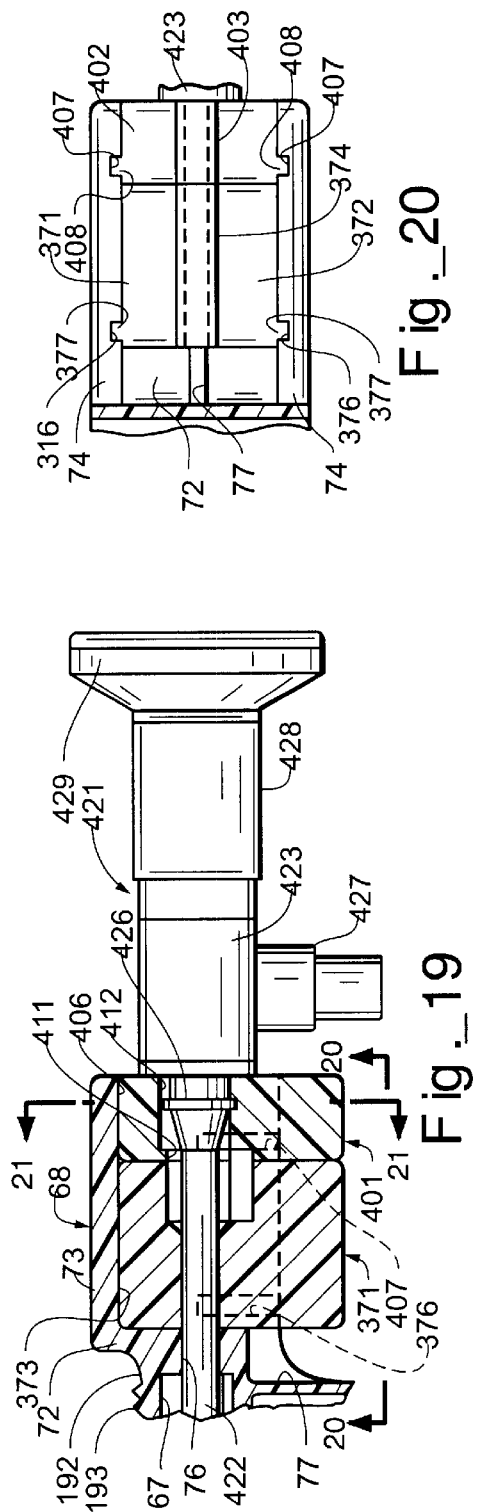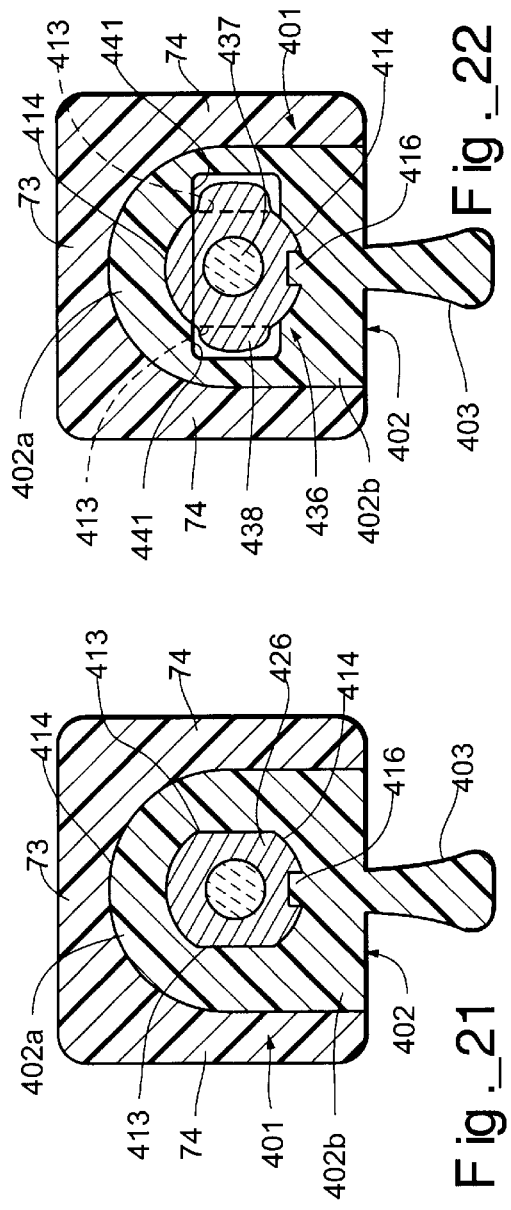

ELECTROSURGICAL DEVICE

This invention pertains generally to medical probe devices for use in natural body openings and, more particularly, to medical probe devices with scopes such as endoscopes for use in electrosurgical procedures.

Medical probe devices such as electrosurgical or electrocautery catheters have heretofore been provided for treating tissue within the human body. These devices, however, suffer from a number of disadvantages. Among other things, many of these devices are limited in purpose. There is therefore a need and improved electrosurgical device which overcomes these disadvantages.

In general, it is an object of the present invention to provide an electrosurgical device which can be adapted for use with a plurality of conventional rod lens endoscopes.

Another object of the invention is to provide an electrosurgical device of the above character which includes a reusable sheath.

Another object of the invention is to provide an electrosurgical device of the above character which includes at least one needle electrode which can be advanced sidewise of the longitudinal axis of the catheter at a selected angle ranging from 0 to 90°.

Another object of the invention is to provide an electrosurgical device of the above character which includes a second needle electrode which can be selectively advanced or not advanced with the first needle electrode.

Another object of the invention is to provide an electrosurgical device of the above character which permits a generally unobstructed view of the needle electrodes advancing toward the target region in the body.

Another object of the invention is to provide an electrosurgical device of the above character which includes guide cannulas provided with T-shaped slots for providing a relatively smooth bend in the guide cannulas.

Another object of the invention is to provide an electrosurgical device of the above character in which a substantially rigid pull/push member is provided in the guide cannulas for bending and straightening of the guide cannulas.

Additional objects and features of the invention will appear from the following description from which the preferred embodiments are set forth in detail in conjunction with the accompanying drawings.

FIG. 1 is a side elevational view, partially cut away, of an embodiment of the electrosurgical device of the present invention adapted for use with a first endoscope.

FIG. 2 is an isometric view of the sheath portion of the electrosurgical device of FIG. 1.

FIG. 3 is a cross-sectional view of the sheath portion of the electrosurgical device of FIG. 1 taken along the line 3—3 of FIG. 2.

FIG. 4 is a cross-sectional view of the sheath portion of the electrosurgical device of FIG. 1 taken along the line 4—4 of FIG. 3.

FIG. 5 is an enlarged view, partially cut away, of the sheath portion of the electrosurgical device of FIG. 1.

FIG. 6 is a cross-sectional view of the electrosurgical device of FIG. 1 taken along the line 6—6 of FIG. 1.

FIG. 7 is an end elevational view of the electrosurgical device of FIG. 1 taken along the line 7—7 of FIG. 1.

FIG. 8 is an enlarged side elevational view, partially cut away, of the distal extremity of the sheath portion of the electrosurgical device of FIG. 1.

FIG. 9 is a cross-sectional view of the electrosurgical device of FIG. 1 taken along the line 9—9 of FIG. 8.

FIG. 10 is a cross-sectional view, similar to FIG. 9, of another embodiment of the electrosurgical device of the present invention.

FIG. 11 is an enlarged side elevational view, similar to FIG. 8 and partially cut away, of the distal extremity of another embodiment of the electrosurgical device of the present invention.

FIG. 12 is a cross-sectional view, similar to FIG. 9, of the electrosurgical device of FIG. 11 taken along the line 12—12 of FIG. 11.

FIG. 13 is a side elevational view of a portion of another embodiment of the electrosurgical device of the present invention.

FIG. 14 is a cross-sectional view of the electrosurgical device of FIG. 1 taken along the line 14—14 of FIG. 1.

FIG. 15 is a cross-sectional view of the electrosurgical device of FIG. 1 taken along the line 15—15 of FIG. 1.

FIG. 16 is a fragmentary cross-sectional view of the electrosurgical device of FIG. 1 taken along the line 16—16 of FIG. 14.

FIG. 17 is a fragmentary cross-sectional view of the proximal portion of the electrosurgical device of FIG. 1 adapted for use with a second cystoscope.

FIG. 18 is a cross-sectional view of the electrosurgical device of FIG. 17 taken along the line 18—18 of FIG. 17.

FIG. 19 is a fragmentary cross-sectional view of the proximal portion of the electrosurgical device of FIG. 1 adapted for use with a third cystoscope.

FIG. 20 is a bottom plan view of the electrosurgical device of FIG. 19 taken along the line 20—20 of FIG. 19.

FIG. 21 is a cross-sectional view of the electrosurgical device of FIG. 19 taken along the line 21—21 of FIG. 19.

FIG. 22 is a cross-sectional view, similar to FIG. 21, of the proximal portion of the electrosurgical device of FIG. 1 adapted for use with a fourth cystoscope.

In general, an electrosurgical device is provided for medical treatment of tissue at a treatment site through a natural body opening. The device includes an elongate probe member having proximal and distal extremities and a sidewall for forming a passage extending from the proximal extremity to an opening at the distal extremity. The elongate probe member is provided with an elongate cutout in the sidewall adjacent the opening so that the elongate probe member is formed with an elongate extension projecting alongside the cutout beyond the opening. A guide canula is mounted in the passage of the elongate probe member and has proximal and distal extremities and a lumen extending therethrough from the proximal extremity to the distal extremity. A radio frequency electrode is disposed in the lumen and an insulating sleeve is coaxially disposed on the radio frequency electrode. A handle is secured to the proximal extremity of the guide canula and means is carried by the handle and secured to the radio frequency electrode and the insulating sleeve whereby the radio frequency electrode and the insulating sleeve can be advanced and retracted with respect to the guide canula. Means is carried by the handle for causing bending of the distal extremity of the guide cannula into the cutout. The extension of the elongate probe member provides support to the guide cannula against the force of the radio frequency electrode engaging the tissue. A method for using the device is provided.

More in particular, electrosurgical device or catheter 21 of the present invention includes sheath means in the form of sheath portion or sheath 22 and handle means in the form of handle portion or handle 23 (see FIG. 1). Electrocautery or electrosurgical catheter 21 is adapted for use with a plurality of different endoscopes such as conventional endoscope 26 made by Olympus Corporation for cystoscopy. Endoscope 26, in general, includes an elongate optical element 27 having proximal and distal extremities 27a and 27b. Optical element 27 has a distal viewing face 28 inclined at an oblique angle of approximately 300 relative to the longitudinal axis of the optical element. Optical element 27 is provided with an axially-extending central rod lens concentrically surrounded by a plurality or bundle of light fibers shown generally and collectively in FIG. 6 and enclosed by a protective rigid tubular sheath made from any suitable material such as stainless steel. Endoscope 26 has a proximal portion which includes lens housing 29 interconnected to proximal extremity 27a of optical element 27 by fitting 31. The fitting 31 is formed with a distally projecting coupling extension 32 and is further provided with a light post 33 for permitting a suitable light source to be connected to the bundle of optical light fibers carried within optical element 27. Lens housing 29 is further provided with an eyepiece 34.

Sheath 22, as illustrated separately in FIG. 2, includes an elongate tubular member or tube 36 having proximal and distal extremities 36a and 36b. Substantially rigid tube 36 can be of any suitable type and size, as for example, a 23 French catheter-like guide housing having a length of approximately nine inches and can be formed of a suitable material such as stainless steel. Tube 36 extends along a central longitudinal axis 37 and has an external or outer cylindrical wall 38 for forming an internal lumen or passageway 39 which extends from proximal extremity 36a to an opening 41 at distal extremity 36b. Passageway 39 is generally oblong in cross-section, as illustrated in FIG. 6, and includes an upper portion 39a and a lower portion 39b.

A locking assembly 46 is mounted to proximal extremity 36a of a tube 36 (see FIGS. 3–5). Locking assembly 46 includes a distal member in the form of a cylindrical member or hub 47 made from any suitable material such as brass and provided with a bore 48 which extends longitudinally therethrough. Bore 48 is generally oblong in cross-section and has an upper portion 48a and a lower portion 48b. The bore 48 has an enlarged distal portion for receiving proximal extremity 36a. The tube 36 is joined to hub 47 by brazing or any other suitable means. Hub 47 has a length of approximately 0.7 inch and is formed with a proximal portion 47a and a distal portion 47b which are each circular in cross-section. Distal portion 47b has an outer diameter of approximately 0.70 inch and proximal portion 47a is of reduced diameter relative to the distal portion 47b with an outer diameter of approximately 0.56.

Locking assembly 46 further includes a proximal member in the form of an optic lock block 51 made from brass or any other suitable material and having proximal and distal end portions 51a and 51b. Block 51 has a length of approximately 1.5 inch. Spaced-apart first and second dowels 52 extend longitudinally from the distal end portion 51b of block 51 and are cooperatively received within similarly spaced-apart first and second longitudinally-extending bores 53 extending into hub proximal portion 47a for assisting in the mounting of block 51 to hub 47. Block 51 extends proximally from hub 47 along longitudinal axis 37 and is joined to the hub by any suitable means such as brazing. The block 51 is provided with a central bore 56 extending between proximal and distal end portions 51a and 51b which communicates with bore upper portion 48a of the hub 47. Stopcock hub 47 and optic lock block 51 are nickel plated to seal the brass material of these elements and to give locking assembly 46 a uniform cosmetic as well as functional outer coating.

Handle 23 is adapted to secure endoscope 26 to sheath 22. The handle 23 has an outer shell 61 made from a suitable material such as polycarbonate and formed from a first or left side portion 61a and a second or right side portion 61b as illustrated in FIGS. 1 and 14. Handle 23 includes coupling means in the form of coupling portion 63 for interconnecting handle 23 to sheath 22 and a depending portion 64 for grasping by a human hand. Coupling portion 63 mounts to the proximal portion of sheath 22 and extends along longitudinal axis 37. Depending portion 63 extends at a right angle to axis 37 when the handle 23 is mounted to sheath 22. Coupling portion 63 has a distal section 66 formed with a longitudinally-extending internal socket 67 which is sized and shaped to cooperatively receive optical lock block 51 with a slip fit. Coupling portion 63 further includes an inverted U-shaped proximal section 68 provided with an internal recess 71 formed by a transversely-extending internal wall 72, a top wall 73 extending proximally from internal wall 72 and spaced-apart first and second side walls 74 extending proximally from the internal wall 72 and depending from the top wall 73. A longitudinally-extending bore 76 extends through internal wall 72 from internal recess 71 into socket 67 and is aligned so as to communicate with central bore 56 of the optic lock block 51.

Internal recess 71 is sized and shaped to cooperatively receive fitting 31 and at least a portion of lens housing 29 of endoscope 26 (see FIG. 1). Fitting 31 abuts internal wall 72 and optical element 27 extends through bore 76 into bore 53 of the optic lock block 51, upper portion 48a of hub bore 48 and upper portion 39a of tube passageway 39.

Internal wall 72 is included within the first adapter means of coupling portion 63 for engaging first coupling extension or coupling extension 32 of endoscope 26. Wall 72 and sheath 22 are longitudinally sized so that distal extremity 27b of the endoscope 26 extends within upper portion 39a of passageway 39 to a point adjacent and generally aligned with tube opening 41. Internal wall 72 is also included within the first cooperative means of coupling portion 63 for mating with coupling extension 32 to restrict rotation of endoscope 26 about longitudinal axis 37. As illustrated in FIGS. 1 and 19, the internal wall 72 is formed with a locking recess 77 which receives endoscope coupling extension 32 and thereby limits rotational movement of the endoscope within coupling portion 63 and sheath 22. First locking recess 77 is angularly aligned about the longitudinal access 37 so that when coupling extension 32 is disposed therein, oblique viewing face 28 is inclined upwardly away from lower portion 39b of passageway 39.

Locking assembly 46 is included within means carried by proximal extremity 36a of tube 36 for gripping optical element 27 to secure endoscope 26 within sheath 22 and thus secure handle 23 to the sheath and endoscope. As illustrated in FIG. 3, proximal end portion 51a of block 51 is provided with an enlarged recess 81 and an annular groove 82 where central bore 56 opens into recess 81. An annular flexible element made from an elastomeric material in the form of optic-lock O-ring 83 is pressed into annular groove 82 and backed by an annular washer-like element in the form of an optic lock washer 84 made from any suitable material such as stainless steel and also disposed within annular groove 82.

Means is included within locking assembly for compressing O-ring 83 so to cause the O-ring to expand against optical element 27. The enlarged recess 81 is sufficiently sized for transversely receiving a clamping member in the form of optic lock yoke 86 made from any suitable material such as stainless steel and provided with a centrally disposed bore 87 extending longitudinally therethrough for receiving endoscope optical element 27 (see FIGS. 3 and 4). Yoke 86 is pivotly retained within recess 81 by a cylindrical pin 91 disposed in a second bore 92 extending through a first end of optic lock yoke 86 in a direction perpendicular to central bore 87. Pin 91 is press fit or otherwise suitably secured at each end within a bore 93 extending through proximal end portion 51a of block 51 and recess 81 provided therein. Yoke 86 is provided with first and second protuberances 96 which are diametrically disposed about a central bore 87 in the yoke. Protuberances 96 extend forwardly from the distal surface of yoke 86 and engage the top and bottom of lock washer 84.

Means is included for pivoting optic lock yoke 86 about the axis of pin 91 and includes an elongate member or drawbar 97, illustrated in FIGS. 3 and 4, made from stainless steel or any other suitable material and having proximal and distal end portions 97a and 97b. Drawbar 97 is disposed in a cooperatively sized second elongate bore 101 extending through optic lock block 51 in parallel disposition to central bore 56 and protrudes into a second similarly aligned and sized bore 102 extending into proximal portion 47a of hub 47 in parallel disposition to bore 48 of the hub. Drawbar proximal end portion 97a is hammerhead in conformation so as to have a narrowed portion 103 for disposition within a cutout 104 formed by spaced-apart first and second extensions on the opposite end of yoke 86 from second bore 92 (see FIG. 4). Proximal end portion 97a of the drawbar 97 rides against the inner wall forming enlarged recess 81 which serves to retain narrowed portion 103 within cutout 104 during axial movement of the drawbar within block 51 and hub 47. An end cap 106 made from nickel plated brass or any other suitable material extends over the opening of enlarged recess 81 and is secured to proximal end portion 51a of block 51 by brazing or any other suitable means. A bore 107 for receiving optical element 27 extends through end cap 106 and is axially aligned with the central bore 56 of block 51.

Means for causing drawbar 97 to slide proximally and distally within optic lock block 51 so as to pivot optic lock yoke 86 includes a first and inner annular member or ring 111 made from stainless steel or any other suitable material. Linear slip ring 111 is diametrically sized so as to slidably extend around hub proximal portion 47a generally flush with hub distal portion 47b (see FIG. 3). Hub proximal portion 47a is provided with an elongate slot 112 which extends alongside the hub into second bore 102. A first radially extending pin 113 extends through the elongate slot 112 and is press fit or otherwise suitably secured at its outer end within a radially extending bore 116 in ring 111 and press fit or otherwise suitably secured at its opposite inner end within a bore 117 extending through distal end portion 97b of the drawbar 97.

Locking assembly 46 includes a second annular member or ring in the form of optic lock collar 121 made from a suitable material such as stainless steel and provided with a central opening 122 extending therethrough. Collar 121 has an internal diameter slightly larger than the external diameters of hub distal portion 47b and slip ring 111 so as to permit the collar to rotatably extend around slip ring 111 and over a portion of hub distal portion 47b. Collar 121 is formed with a proximal flange 123 which extends inwardly into opening 122 and is internally sized for rotatable disposition about hub proximal portion 47a. A radial bore 126 is provided in collar 121 and a radially-extending lever or radius bar 127 is threaded or otherwise suitably secured within bore 126. Radius bar 127 includes a radial extension 128 which extends inwardly into central opening 122 through a helically-extending slot 131 provided in linear slip ring 111 and into a circumferentially-extending slot 132 provided in hub proximal portion 47a. The disposition of radial extension 128 in slot 132 of hub proximal portion 47a longitudinally fixes optic lock collar 121 relative to hub 47.

As can be appreciated by those skilled in the art, rotation of collar 121 relative to hub 47, by means of radius bar 127 or otherwise, causes bar extension 128 to move through helical slot 131 to thus cause linear slip ring 111 trapped between collar 121 and hub proximal portions 47a to move longitudinally relative to the collar 121 and hub 47. Slip ring 111 is longitudinally Ad sized smaller than hub proximal portion 47a to permit travel of the slip ring over the proximal portion 47a. By so causing slip ring 111 to move toward hub distal portion 47b, yoke protuberances 96 are pressed against washer 84 under the force of drawbar 97 so as to compress O-ring 83 and cause it to expand radially inwardly and circumferentially grip optical element 27 of endoscope 26. A second radially extending pin 136 press fit or otherwise suitably secured within a radially provided bore 137 in hub proximal portion 47a and projecting outwardly into a longitudinally-extending slot 138 formed in linear slip ring 111 further assists in restricting rotation of slip ring 111 relative to hub 47.

First and second stopcocks 141 and 142 are provided on sheath 22 for permitting any suitable liquid such as a flushing fluid to be introduced into and withdrawn from sheath passageway 39. The stopcocks 141 and 142 can be of any conventional type such as those made by Popper and Sons of New Hyde Park, N.Y. Distal portion 47b of hub 47 is provided with first and second radially extending bores 143 and 144 which extend into hub bore 48. The first and second stopcocks 141 and 142 are attached to hub distal portion 47b so as to communicate with respective first and second bores 143 and 144 and thus tube passageway 39. The bores 143 and 144 extend along a diameter of hub 47 and the stopcocks 141 and 142 are on opposite sides of sheath 22. Optic lock O-ring 83 additionally serves as a fluid tight seal within optic lock block 51 to prevent flow of flushing fluid proximally of the O-ring 83.

At least one and as shown in FIGS. 6 and 7 first or left stylet 146 and second or right stylet 147 are disposed within respective first or left guide cannula 148 and second or right guide cannula 149 carried by handle 23 for slidable disposition within passageway 39 of sheath 22. More specifically, guide cannulas 148 and 149 are slidably mounted in side by side disposition in lower portion 39b of bore 48 adjacent and below optical element 27. The guide cannulas are fastened together by any suitable means such as solder 151. Left and right guide cannulas 148 and 149 are identical in structure and each include an outer guide tube 152 made from a suitable material such as stainless steel having outside and inside diameters of approximately 0.072 and 0.062 inches and a length of approximately 10.5 inch. Guide tubes 152 are provided with proximal and distal extremities 153 and 154 and a central passage or lumen 155 extending between extremities 153 and 154. Proximal extremities 153 are each provided with a flange 156.

A plurality of circumferentially-extending T-shaped slots 157 are longitudinally spaced-apart along distalmost portion 154a of distal extremity 154 of each guide tube 152 for adding flexibility to flexible portion 154a (see FIG. 8). Each slot 157 subtends an angle less than 360° and has a transverse portion 157a with a suitable width ranging from approximately 0.012 to 0.016 inch. Slots 157 are not offset radially and therefore provide a backbone or rib 161 extending longitudinally of guide tube 152. Rib 161 has a width in the proximalmost-slot 157 ranging from 0.012 to 0.016 inch and tapers in width as it extends distally to a width at the distalmost slot ranging from approximately 0.007 to 0.011 inch.

Flanges 156 are included within the means of electrosurgical catheter 21 for securing left and right guide cannulas 148 and 149 to handle 23. As illustrated in FIG. 1, handle shells 61 are formed with an internal cavity 166 and a passage 167 which extends from cavity 166 to an opening adjacent socket 67. The proximalmost portion of guide tube proximal extremities 153 are disposed within passage 167 and the passage includes an enlarged portion 168 which is sized and shaped to snugly receive flanges 156 so as to restrict longitudinal movement of the guide tube cannulas 148 and 149 within passage 167. Guide tubes 152 can be secured within passage 167 by any suitable means such as an adhesive (not shown). The passage 167 is aligned so that left and right guide cannulas 148 and 149 extend outwardly from handle 23 and distally through lower portion 48b of hub bore 48 into lower portion 39b of tube passageway 39 when sheath 22 is mounted to handle 23. Guide tubes 152 have a length so that distalmost portions 154a extend beyond tube opening 41 and viewing face 28 of endoscope 26.

Distal extremity 36b of tube 36 is provided with a cutout 171 for forming tube opening 41 and an elongate tube extension 172 from tube outer or sidewall 38 (see FIGS. 2, 7 and 8). Cutout 171 causes upper portion 39a of tube passageway 39 to terminate at opening 41. Tube extension 172, which is generally U-shaped in cross-section as shown in FIG. 7, is formed with spaced-apart flared side portions 173 which serve to receive and support distalmost portions 154a of guide tubes 152. Extension 172 has a length greater than that of distalmost portions 154a so that left and right guide cannulas 148 and 149 do not extend longitudinally beyond the tube extension 172.

Means for actuating the bending and/or straightening of distalmost portion 154a of each guide tube 152 includes an elongate actuation element or ribbon 176 made from any suitable materials such as stainless steel and having proximal and distal end portions 176a and 176b. Substantially rigid ribbon 176 has a cross-section which inhibits bending of the ribbon when placed under axial compression. It is preferable that ribbon 176 has a cross-sectional configuration with a width W greater than its thickness T. In the embodiment of ribbon 176 illustrated in FIG. 6, the ribbon is generally planar so as to be a strip and has a width of approximately 0.030 inch and a thickness of approximately 0.007 inch.

Ribbon 176 is relatively snugly disposed or sandwiched between the inside of guide tube 152 and the respective stylet 146 and 147 carried therein so as to further inhibit bending of the ribbon when placed under compression. Distal end portion 176b of ribbon 176 is secured to the inside of guide tube 152 distally of portion 154a by any suitable means such as solder 177 (see FIG. 9). Ribbon 176 is attached to the inside of the guide tube in diametric opposition to rib 161 and stretches the length of the guide tube 152. Each ribbon 176 extends from proximal extremity 153 of the respective guide tube into internal cavity 166 of handle 23 where the ribbons connect to an actuation or lever assembly 181.

Lever assembly 181, illustrated in FIG. 1, serves to simultaneously move first and second ribbons 176 proximally and distally within respective left and right guide cannulas 148 and 149. The lever assembly 181 includes a rod or shaft 182 made from a suitable material such as stainless steel and rotatably mounted within a bore 183 extending transversely through handle 23. Shaft 182 is provided with a bore-like recess 186 extending longitudinally along the outside thereof for receiving a stainless steel pin 187 to which the proximal end portions 176b of first and second ribbons 176 are spot welded or otherwise suitably secured in spaced-apart disposition. A plastic U-shaped lever element or lever 191 extends over the top of coupling portion 63 and is secured to each end of pivot shaft 182. Lever 191 has a transversely-extending portion 191a which travels within a cutout 192 provided at the top of coupling portion 63 above socket 67 and the coupling portion is further provided with a plurality of transversely-extending generally parallel spaced-apart detents 193 for indexing the lever 191 as it travels proximally and distally through cutout 192.

Lever 191 rotates through an angle of approximately 45° as it pivots about the axis of shaft 182 from a first position shown in solid lines in FIG. 1 in which distalmost portions 154a are generally straight and a second position shown in phantom lines in FIG. 1 in which distalmost portions 154a are fully bent as shown in phantom lines in FIGS. 1 and 8. Shaft, 182 is circumferentially sized so that 45° rotation of the shaft causes ribbons 176 to bend distalmost portions 154a of guide tubes 152 through an angle of approximately 0 to 90°. Detents 193 can be positioned to correspond with particularly desirable angles within this range. Ribbons 176 are circumferentially placed on guide tubes 152 so that left and right guide cannulas 148 and 149 bend apart at an angle of approximately 40° (see FIG. 7). Although the disclosed and illustrated lever assembly 181 causes distalmost portions 154a of guide cannulas 148 and 149 to always bend together, it should be appreciated that lever assembly could be segmented to permit individual bending of the distal ends of the guide cannulas and be within the scope of the present invention.

The elongate actuation elements or ribbons for articulating left and right guide cannulas 148 and 149 can have other rigidity enhancing configurations for permitting their use under compressive forces and be within the scope of the present invention. For example, an elongate actuation element such as actuation element 201 illustrated in FIG. 10 could be utilized. Actuation element 201 has a cross-sectional which is arcuate in shape. The curvature of actuation element 201 adds to the buckling strength of the ribbon.

A tubular actuation element can also be provided. For example, a tubular actuation element or tube 206 made from any suitable material such as stainless steel can be provided as illustrated in FIGS. 11 and 12. Actuation tube 206 is transversely sized so as to concentrically extend around the stylet within the guide tube 152 and has a distal extremity 207 with an outside diameter of approximately 0.059 inch and an inside diameter of approximately 0.052 inch. Distal extremity 207 is provided with a plurality of circumferentially-extending T-shaped slots 208 substantially similar to T-shaped slots 157 and longitudinally spaced apart along the distalmost portion 211 of actuation tube distal extremity 207 at approximately equal distances. Slots 208 are not offset radially about the longitudinal axis of actuation tube 206 and therefore provide a backbone or rib 212 extending longitudinally along the actuation tube 206. Rib 212 can have a constant width or be tapered as it extends distally in a manner similar to rib 161 of guide tube 152. Actuation tube 206 is angularly aligned within guide tube 152 so that its rib 212 is diametrically opposed to rib 161 of guide tube 152. The number of T-shaped slots 208 in actuation element 206 does not necessarily have to conform to the number of T-shaped slots 157 in guide tube 152 although in the embodiment of electrosurgical catheter 21 illustrated in FIG. 11, the number of T-shaped slots 157 and 208 are equal.

In yet another alternative embodiment of the elongate actuation element of the present invention, a tubular actuation member or tube 216 is provided which is substantially similar in composition and size to actuation tube 206. Actuation tube 216, illustrated in side elevational plan in FIG. 13, has a distal extremity 217 provided with an elongate cutout 218 which forms a linear rib 219 extending longitudinally of the actuation tube 216. Rib 219 has a width substantially the same as rib 212 of actuation tube 206 and an actuation tube 216 is angularly aligned within each guide tube 152 around the stylet therein so that rib 219 is aligned with and generally extends over rib 161 of the guide tube 152.

Actuation tubes 206 and 216 are each secured to the guide tube 152 and actuated in substantially the same manner. In this regard, an actuation tube 206 or 216 is secured at its distal end to the end of each guide tube 152 distal of T-shaped slots 157. The actuation tubes 206 and 216 have respective proximal extremities (not shown) which are substantially similar to rib 161. These proximal extremities are secured to lever assembly 181 in the same manner as rib 161 for bending and straightening of the guide tubes 152.

Left and right stylets 146 and 147 are substantially identical in construction and each include a flexible elongate radio frequency electrode 226 formed from a suitable conductive material such as a nickel titanium alloy having superelastic properties so that the needle electrode returns to its original configuration after being bent as hereinafter described. Each needle electrode 226 has a proximal extremity 226a and a distal extremity 226b with a sharpened distal tip 227. Electrodes 226 each have an external diameter of approximately 0.018 inch. A flexible tube member or sleeve 231 made from any suitable insulating material such as nylon is coaxially carried about each needle electrode 226. Each insulating sleeve 231 has a proximal extremity 231a and a distal extremity 231b and is formed with first and second passageways or lumens 232 and 233 which extend longitudinally the length thereof. Second lumen 233 is closed at its distal end. Insulating sleeves 231 are each oval-shaped in cross-section and each have outer transverse dimensions of approximately 0.010 by 0.034 inch. First lumens 232 each have an inner diameter of approximately 0.021 inch.

First and second elongate tubular members or control tubes 236 serve to couple first and second insulating sleeves 231 and internally carry first and second needle electrodes 226 to handle 23 of electrosurgical catheter 21. Control tubes 236 are each made from any suitable material such as stainless steel and have proximal and distal extremities 236a and 236b. A central bore 237 extends longitudinally the length of each control tube 236. Each control tube 236 is externally sized to fit within first lumen 232 of the respective sleeve 231 and extends substantially the entire length of the sleeve for adding compressive or buckling strength to the sleeve. The insulating sleeve 231 is stretched and annealed so as to shrink about the control tube 236 and thus secure the insulating sleeve to the control tube. Each sleeve 231 is longitudinally sized so that it precludes electrical contact between the respective control tube 236 and guide cannula 148 or 149 at all times.

First and second temperature sensing or sensor means in the form of first and second thermocouples 241 and 242 are carried by the distal extremity 231b of each insulating sleeve 231. First and second thermocouples 241 and 242 are each disposed within second lumen 233 respective distances of approximately one millimeter and six millimeters from the distal end of the insulating sleeve. Two first leads 243 are electrically connected to first thermocouple 241 and two second leads 244 are electrically connected to second thermocouple 242. First and second leads 243 and 244 extend through second lumen 233 the length of the insulating sleeve 231 to proximal extremity 231a thereof.

Operative means in the form of first or left actuation assembly 251 and second or right actuation assembly 252 is carried by sheath 22 and included within handle 23 for causing respective left and right stylets 146 and 147 to move distally and proximally within respective left and right guide canulas 148 and 149 (see FIGS. 1 and 14–16). Actuation assemblies 251 and 252 are aligned side by side within cavity 166 of handle shell 61 and each pivot when engaged with a shaft element or shaft 253 disposed substantially perpendicular to the actuation assemblies and extending transversely through handle depending portion 64 perpendicular to longitudinal axis 37. Left actuation assembly 251 includes a first or left needle electrode and insulating sleeve drive element 256 and right actuation assembly 252 includes a second or right needle electrode and insulating sleeve drive element 257. Drive elements 256 and 257 are each generally planar in confirmation and made from any suitable material such as polycarbonate. The drive elements 256 and 257 are substantially identical in structure and operation except that left drive element 256 is provided with a finger actuation element or lever 258 which extends from cavity 166 through an opening 259 in shell 61.

Drive elements 256 and 257 are provided with transversely aligned bores 261 for receiving pivot shaft 253. Each of bores 261 is square in cross-section, as illustrated in FIG. 16 with respect to right actuation assembly 252. Shaft 253 has an opposite first or left end portion 253a and a second or right end portion 253b which are each circular in cross-section and rotatably received within transversely aligned bores 262 in left and right shell side portions 61a and 61b (see FIG. 14). shaft 253 is longitudinally sized so as to extend beyond the outside of right side portion 61b at all times and a lever 266 is rotatably mounted about shaft right end portion 253b.

Means which includes shaft 253 is included within electrosurgical catheter 21 for selectively engaging and disengaging right actuation assembly 252. Shaft 253 is further provided with a first or left torque transmitting portion 253c and a second or right torque transmitting portion 253d which are each square in cross-section, as illustrated in FIGS. 14 and 16 with respect to right square portion 253d, and a central portion 253e which is circular in cross-section and thus similar to end portions 253a and 253b.

Shaft 253 is movable longitudinally between a first or fully engaged position illustrated in FIG. 14 in which right square portion 253d is disposed within bore 261 in right drive element 257 and a second or partially engaged position, not illustrated, in which right square portion 253d has been moved out of the bore 261 in right drive element 257 into a central space between the drive elements 256 and 257. Left square portion 253c is longitudinally sized so as to remain within bore 261 of left drive element 256 when shaft 253 is in each of its first and second positions. Shaft 253 and bore 267 in lever 266 are longitudinally sized so that shaft right end portion 253a extends into the lever 267 in each of its first and second positions. The shaft 253 is further provided with an integral longitudinally-extending left pin 271 having a plastic cover or cap 272 secured thereto for manually moving the shaft to its fully engaged position and a similar right pin 273 having a plastic cover or cap 274 secured thereto for manually moving the shaft to its partially engaged position. Travel of shaft 253 is limited by the engagement of caps 272 and 274 with handle shell 61. Thus, right actuation assembly 252 can be engaged or disengaged relative to left actuation assembly 251 by merely moving shaft 253 between its fully engaged and partially engaged positions.

Each of actuation assemblies 251 and 252 includes means for securing proximal extremity 226a of the respective needle electrode 226 thereto so that the needle electrode moves longitudinally within guide tube 152 as respective drive element 256 or 257 rotates with shaft 253. As illustrated in FIG. 1 with respect to left actuation assembly 251, each drive element 256 and,257 includes a retainer 276 formed integral therewith. Retainer 276 includes a recess 277 for cooperatively receiving and securing an enlarged connector 278 electrically coupled and secured to the proximal end of the needle electrode 226. Connector 278 is mounted within recess 277 to move with the drive element about the axis of shaft 253.

Means is provided for pivotly coupling each of the insulating sleeves 231 to its respective drive element 256 or 257 and includes an insulating sleeve return element or hood 281 made from any suitable material such as polycarbonate (see FIGS. 1, 14 and 15). Each hood 281 is generally U-shaped in conformation and is formed with spaced-apart first and second sidewalls 282 interconnected by an arcuately-extending outer wall 283 as shown in FIG. 14. Sidewalls 282 and outer wall 283 form an inner space 284. The hood is pivotally connected to the drive element by a pin 286 so that a portion of the drive element extends inside of the hood 281. A transversely extending recess 287 is provided at the outer rear portion of arcuate outer wall 283 and is sized so as to cooperatively receive a rod-like member 291 secured to the proximal end of the respective control tube 236. Rod member 291 is made from any suitable material such as stainless steel and is secured to the control tube by a suitable means such as soldering. A bore 292 extends diametrically through rod member 291 and communicates with bore 237 of the control tube. Proximal extremity 226a of the respective needle electrode 226 slidably extends from control tube bore 237 through rod member bore 292. Thus, pivoting of hood 281 about pin 286 causes the insulating sleeve 231 carried by the control tube 236 to move longitudinally relative to the respective needle electrode 226.

Relative movement between a drive element 256 or 257 and handle shell 61 and between a hood 281 and its respective drive element 256 or 257 can now be described with respect to left actuation assembly 251 illustrated in side elevational plan in FIG. 1. Left drive element 256 is movable between a first or home position shown in solid lines in FIG. 1 and a second or actuated position (not shown) to which the drive element would pivot about shaft 253 in the direction identified by reference numeral 288 in FIG. 1. When the left drive element 256 is in its illustrated home position, left needle electrode 226 is fully retracted within left guide cannula 148. When the left drive element 256 is in its fully actuated or counterclockwise most position, the needle electrode 226 extends from left guide cannula 148 a predetermined distance ranging from 10 to 22 millimeters.

Left hood 281 is rotatable about pin 286 between a first or extended position, shown in solid lines in FIG. 1, and a second or retracted position (not shown). Clockwise rotation of hood 281 relative to left drive element 256 is limited by the engagement of internal stop 296 extending inwardly from one of sidewalls 282 into inner space 284 with forward surface 297 of the drive element or the earlier engagement of hood outer wall 283 with stop 298 formed integral with handle shell 61.

Each hood 281 is biased toward its retracted position by a coil spring 303 disposed within a recess 304 in the drive element and secured at one end to a hook 307 formed on the drive element 256 and at the other end to a retaining pin 308 extending transversely through inner space 284 and connected at its ends to spaced-apart side walls 282 (see FIGS. 1 and 15). An arcuately shaped opening 309 is formed in drive element 256 and extends into recess 304 to permit travel of the retaining pin 308 as hood 281 moves between its two positions.

Means is provided for retaining each hood 281 in its extended position under the force of coil spring 303 and includes a flexible stop 316 formed integral with one of thin sidewalls 282 by means of a U-shaped opening 316 formed in the sidewall (see FIG. 1). Flexible stop 317, as illustrated in FIG. 15 with respect to left actuation assembly 251, includes a hinge 318 and an extension 321 formed with a forward surface 322 extending inwardly from the outer surface of sidewall 282 at an approximately right angle and a ramped surface 323 extending at an oblique angle from the inner surface of the sidewall to join the protruding end of forward surface 322. The drive element 256 is provided with a first cutout 326 which terminates at a limit wall 327 projecting outwardly from the drive element at an approximately right angle. Extension 321 extends into first cutout 326 and the engagement of forward surface 322 of stop 316 with limit wall 327 restricts clockwise rotation of the hood 281 relative to the left drive element 256.

A U-shaped plunger element or plunger 331 made from plastic or any other suitable material is included with each of actuation assemblies 251 and 252 and is included within the means for releasing and unlocking hood 281 to permit the hood to move to its retracted position. As illustrated in FIGS. 1, 14 and 15, plunger 331 is formed with spaced-apart, parallel guide portions 332 and engagement wall 333 extending therebetween. The front portion of the drive element 256 or 257 is formed with a second opposite cutout 336 opposite first cutout 326. The cutouts 326 and 336 cooperatively receive guide portions 332 and form a central rail 337 which extends between the guide portions 332. A slot 338 extends through central rail 337, as illustrated in FIG. 14, and an elongate coil spring 341 is disposed within slot 338 for biasing plunger 331 away from limit wall 327 (see FIG. 15). Relative movement between plunger 331 and central rail 337 against the force of coil spring 341 causes one of guide portions 332 to engage ramped surface 323 of flexible stop 316. Further movement of the plunger 331 along ramped surface 323 causes flexible stop 316 to pivot outwardly at hinge 318 and thus cause extension 321 to disengage from limit wall 327. The ultimate engagement of plunger 331 with limit wall 327 precludes further actuation of the drive element.

Adjustable means is provided for engaging the U-shaped plungers 331 as actuation assemblies 251 and/or 252 are pivoted upwardly in cavity 166 about the axis of shaft 253. This adjustment means includes a generally rod-like cross member 346 made from plastic or any other suitable material extending transversely through internal cavity 166 of shell 61 (see FIG. 14). Left and right shell side portions 61a and 61b are provided with aligned arcuately-extending first and second slots 347 for receiving the ends of cross member 346 and causing plunger 321 to engage the cross member 346 as the respective drive element is actuated (see FIG. 1). Slots 347 are shaped and positioned on shell 61 so that the release point of hood 281 during the actuation of one or both of drive elements 256 and 257 can be adjusted. Cross member 346 is provided with end caps 348 on each end for retaining the cross member within slots 347 and facilitating adjustment of the cross member relative to graduations (not shown) which can be provided on the outside of shell 61. Engagement wall 333 of each U-shaped plunger 331 is provided with an inclined outer surface 349. When the plunger 331 engages cross member 346 the resultant force exerted on the cross member 346 by the inclined surface 359 is in a direction generally perpendicular to the direction of arcuate slots 347. In this manner, drift of the cross member through slots 347 is minimized if not eliminated.

Lever 266 is included within the means of handle 23 for adjusting the position of cross member 346 in slots 347 (see FIG. 14). Lever 266 is formed with an integral extension 351 which extends through a slot 352 provided in shell right side portion 61b (see FIG. 16). Slot 352 is generally arcuate in shape and extends around a portion of the bore 262 in right side portion 61b. Cross member 346 is formed with an integral flexible tail 353 depending at an approximately right angle from the center thereof between left and right actuator assemblies 251 Rand 252 (see FIGS. 1 and 14). Tail 353 includes an end portion 353a which wraps partially around the center of shaft 253 and is formed with a C-shaped clasp 354 which snaps around the end of extension 351. Thus, movement of extension 351 downwardly through slot 352 by the rotation of lever 266 about shaft 253 pulls cross member 346 downwardly in arcuate slots 347.

A cable 361 terminating in a connector 362 is removably connected to a printed circuit board 363 carried within shell cavity 166 at the bottom of handle 23 for permitting electrical connections between left and right needle electrodes 222 and first and second thermocouples 241 and 242 carried by each of left and right stylets 146 and 147. Electrosurgical catheter 21 can be provided a microchip 364 on printed circuit board 363 for monitoring the usage of electrosurgical catheter 21. Microchip 364 can, for example, be of the type which measures the time during which radio frequency energy is passing through needle electrodes 226 and which renders the catheter electrically or otherwise unusable after the catheter usage reaches a predetermined level. Wires 366 serve to electrically connect proximal extremities 226a of needle electrodes 226 with circuit board 363 and additional wires (not shown) serve to electrically connect first and second leads 243 and 244 from thermocouples 241 and 242 to the circuit board 363. Cable 361 and connecter 362 permit electrosurgical catheter 21 to be used with a conventional radio frequency generator and controller 367 as illustrated in FIG. 1.

Left and right side portions 61a and 61b of handle shell 61 are formed with an opening 368 at the bottom of depending portion 64 which is sized and shaped to receive a finger such as the thumb of a human hand. Opening 368 and finger lever 258 serve to form scissor-type grip on electrosurgical catheter 21.

Handle 23 of electrosurgical catheter 21 includes removable additional or second adapter means in the form of first plug 371 for adapting electrosurgical catheter 21 for use with a second conventional endoscope as illustrated in FIG. 17. First plug 371 mounts to coupling portion 63 of the handle 23 and is formed with a body 372 which is sized and shaped to snugly fit within distal part 373 of internal recess 71 (see FIGS. 17, 18 and 20). Body 372, when viewed in cross-section as in FIG. 18, has a rounded top portion 372a and a squared-off bottom portion 372b. A longitudinally-extending tail or tab 374 depends from the center of body 372 and flares outwardly from bottom portion 372b to facilitate its grasping by the fingers of a human hand. Cooperative mating means is carried by body 372 and handle proximal section 68 and includes opposed first channels 376 formed on the bottom portion of sidewall 74 along the inside adjacent internal wall 72 (see FIGS. 17 and 20). Channels 376 extend in directions perpendicular to longitudinal axis 37. Oppositely extending ridges 377 are formed along bottom portion 372b for slidably engaging first channels 376 when first plug 371 is pushed upwardly into distal part 373 of internal recess 71 adjacent internal wall 72.

First plug 371 is longitudinally sized and provided with suitable cooperative mating means for permitting catheter 21 to be used with a conventional rod lens endoscope 381 of the type manufactured by Circon ACMI. Endoscope 381, a portion of which is shown in FIG. 17, includes an optical element 382 with a distal viewing face (not shown). Optical element 382 is connected to a lens housing 383 having an eyepiece 384 by a fitting 386 provided with a light post 387. Fitting 386 includes a conventional coupling extension 388. Plug 371 is provided with a longitudinally-extending bore 391 through bottom portion 372b for receiving optical element 382 of endoscope 381 and a recess in the form of channel 392 extending along the bottom of a portion of bore 391 for snugly receiving coupling extension 388 (see FIG. 18). Plug 371 is longitudinally sized and shaped so that endoscope fitting 386 abuts the plug 371 when optical element 382 extends through bore 391 into lower portion 39b of sheath passageway 39 and the viewing face of optical element 382 is disposed adjacent passageway opening 41 in substantially the same position as illustrated in FIG. 1 with respect to viewing face 28 of endoscope 26. The snug disposition of coupling extension 388 in channel 392 restricts rotation of endoscope 381 about longitudinal axis 37. Endoscope 381 is secured within sheath 22 by locking assembly 46 in the same manner as discussed above with respect to endoscope 26.

Third or additional adapter means in the form of second lug 401 is included within coupling portion 63 of electrosurgical catheter 21 for permitting the catheter to be used with yet other conventional endoscopes. Second plug 401, which is illustrated in FIGS. 19–22, has a cross-sectional shape similar to first plug 371 and includes a body 402 having a rounded or dome-like top portion 402a and a squared-off bottom portion 402b. A tab 403 similar to tab 374 of first plug 371 depends from the center of bottom portion 402b of the body 402. Second plug 401 has a size and shape to permit its insertion into proximal part 406 of internal recess 71. Additional cooperative mating means is carried by proximal section 68 and plug 401 for removably securing the plug within proximal part 406. In this regard, proximal section 68 is provided with opposed second channels 407 which are substantially similar to first channels 376. Oppositely extending elongate protuberances or ridges 408 substantially similar to ridges 377 are formed on each side of bottom portion 372b for snug disposition within channels 407.

Plug body 402 is provided with a central bore 411 opening into an enlarged recess 412 illustrated in cross-section in FIG. 21. As shown therein, enlarged recess 412 is formed from spaced-apart generally parallel opposed first and second side surfaces 413 and arcuately extending opposed top and bottom surfaces 414 so as to be generally elongate or oblong in cross-sectional shape. A ridge 416 projects upwardly from the center of bottom surface 414 and extends along the length of enlarged recess 412.

Second plug 401 permits electrosurgical catheter 21 to be used with a conventional endoscope 421 such as the type manufactured by Wolf. Endoscope 421, a portion of which is shown in FIG. 19, includes an elongate longitudinally-extending optical element 422 having a distal extremity with a viewing face (not shown) and a proximal extremity mounted to a fitting 423. A coupling extension 426 extends distally from fitting 423 and a light post 427 extends from the fitting at an approximate right angle. A lens housing 428 with an eyepiece 429 is connected to fitting 423 and forms the proximal portion of endoscope 421. Second plug 401 is longitudinally sized so that when fitting 423 abuts the second plug 401 and optical element 422 extends through central bore 411, first plug 371 and sheath 22, the distal viewing face of the optical element 422 is positioned adjacent sheath distal opening 41 similar to viewing face 28 of endoscope 26 as illustrated in FIGS. 1 and 8. Enlarged recess 412 is configured to receive coupling extension 426 of endoscope 421 and has a cross-sectional shape which generally corresponds to the cross-sectional shape of the coupling extension 426 so that endoscope 421 is precluded from rotating about longitudinal axis 37 of electrosurgical catheter 21. Locking assembly 46 serves to secure endoscope 421 within electrosurgical catheter 21.

Second plug 401 further permits electrosurgical catheter 21 to be utilized with a conventional endoscope 436 of the type manufactured by Karl Storz of Germany (see FIG. 22). Endoscope 436 is substantially similar to endoscope 421 and includes an elongate of rod-lens 437 extending from a fitting (not shown) and an optical element (not shown) projecting distally from the fitting. A coupling extension 438 extends distally from the fitting. Second plug 401 is formed with generally rectangular-shaped cutouts 441 which open onto side surfaces 413 and the proximal surface of plug 401. When endoscope 436 is mounted to electrosurgical catheter 21, its fitting generally abuts second plug 401 in the same manner as fitting 423 of endoscope 421 shown in FIGS. 19 and 20 and rod lens 437 extends through central bore 411 of the second plug 401, through first plug 371 and through upper portion 39a of sheath passageway 39. Actuation of locking assembly 46 serves to secure endoscope 436 to the catheter 21.

Second plug 401 is longitudinally sized so that the second plug, together with first plug 371, causes the distal viewing face of endoscope 436 to extend through passageway 39 to a point adjacent opening 41 in a manner similar to that illustrated in FIGS. 1 and 8 with respect to endoscope 26. Coupling extension 438 is snugly received within enlarged recess 412. Cutouts 441 of the enlarged recess 412 and central ridge 416 are included within the additional or second cooperative mating means of second plug 401 for precluding endoscope 436 from rotating about longitudinal axis 37 of electrosurgical catheter 21.

In operation and use, adjustable electrosurgical cartridge (AEC) or handle 23 of the present invention can be used for performing an electrosurgical procedure on tissue at a treatment site within a human body. Handle 23 is mounted to sheath 22 by inserting left and right guide cannulas 148 and 149 carrying left and right stylets 146 and 147 through lower portion 48b of hub bore 48 so that the guide canulas 148 and 149 extend down lower portion 39b of sheath passageway 39. As distal extremities 154 of left and right guide tubes 152 approach tube opening 41, optic lock block 51 is inserted into socket 67 of handle shell 61. When the block 51 is fully disposed within socket 61, distalmost portions 154a of guide tubes 152 are disposed within tube extension 172 beyond opening 141.

The operating physician selects one of four conventional endoscopes 26, 381, 421 or 436 and mounts the appropriate adapter plugs 371 and/or 401, if necessary, to proximal section 68 for use with the selected endoscope. The optical element of the endoscope is inserted through internal recess 71 and any plugs 371 and 401 disposed therein and then into sheath 22 so that the optical element extends through central bore 56 of optic lock block 51, upper portion 48a of hub bore 48 and upper portion 39a of tube passageway 39. Actuation of locking assembly 36 by rotation of optic lock collar 121 via radius bar 127 causes O-ring 83 to compress inwardly against the optical element and secure the optical element within block 51. Coupling portion 63 of handle 23 is precluded from separating from sheath 22 once the endoscope is so secured to sheath 22.

A suitable light source is connected to the light post of the endoscope and radio frequency generator and controller 367 is connected to cable 361. A source of a suitable flushing fluid such as a saline solution is coupled to first and second stopcocks 141 and 142 to permit introduction and/or withdrawal of a saline solution or other fluid through passageway 39 during the procedure.

Catheter sheath 22 is adapted for insertion into a natural body opening for performing a procedure. In one possible procedure, catheter 21 can be inserted into the urethral canal or urethra of a human male for performing an operation on the bladder. When inserting catheter 21 into the urethra, the operating physician grasps handle 23 by inserting his or her thumb through handle opening 368 and wrapping his or her other fingers around finger lever 258. While viewing through the endoscope, the operating physician can grasp the penis and insert tube distal extremity 36b into the urethra. Tube distal extremity 36b and tube extension 172 formed thereon are generally blunt so as to permit the tube 36 to easily pass through the urethra to the bladder without harming the urethral wall. The introduction of the flushing fluid through passageway 39 alongside the optical element and guide cannulas 148 and 149 facilitates viewing of the inside of the urethra and body during placement of tube distal extremity 36b therein. Once electrosurgical catheter 21 has been properly positioned within the body, the operating physician can cause distalmost portions 154a of the guide tubes of left and right guide cannulas 148 and 149 to be bent to a desired angle between 0 and 90° relative to longitudinal axis 37 through movement of lever 191 of lever assembly 181. Detents 193 provided on the top of handle coupling portion 63 facilitate bending of the guide cannulas to the desired angle. T-shaped slots 157 provided in distalmost portion 154a of left and right guide tubes 152 permit relatively smooth bending of the guide tube. In the illustrated and described T-shaped slots 157, longitudinal portions 157b of the slots extend from each side of slot transverse portion 157a so as to more evenly distribute bending and minimize undesirable sharp edges extending into the central lumen or passage of the guide tubes. Any such sharp could snag the stylets slidably extending inside guide tubes 152.

Either one or both of left and right needle electrodes 226 can be extended from guide cannulas 148 and 149 for performing the electrosurgical procedure. In this regard, the operating physician positions shaft 253 so that either left actuation assembly 251 only or both left and right actuation assemblies 251 and 252 are in an engaged position. After the operating physician moves lever 266 to desirably positioned cross member 346 and has rotated catheter 21 about longitudinal axis 37 to a desired position in the urethra, the operating physician pulls on finger lever 258 to cause the engaged drive elements 256 and/or 257 to pivot with shaft 253 relative to handle 23. During this drive stroke, each engaged needle electrode 226 and associated insulating sleeve 231 moves distally through its guide tube 152 and exits distalmost portion 154a of the guide tube. The insulating sleeve is distanced approximately one millimeter behind the sharpened distal tip 227 of the needle electrode 226 prior to the engagement of plunger 331 with cross member 346. Full retraction of finger lever 258 causes the engaged needle electrode 226 to extend a predetermined distance ranging from 10 to 20 millimeters from the end of the guide tube 152.

The placement of cross member 346 within arcuate slots 347 determines when each engaged plunger 331 releases its associated flexible stop 316 so as to cause the hood 281 to pivot backwardly relative to the associated drive element and thus cause the insulating sleeve 231 of the engaged stylet to automatically retract relative to the associated needle electrode 226. The retractable pivoting of hood 281 relative to the associated drive element is limited by hood stop 296 engaging forward surface 297 of the drive element. Handle 23 is constructed so that the engagement of stop 296 and surface 297 results in distal extremity 231b of insulating sleeve 231 extending a predetermined distance of approximately six millimeters from the end of guide tube 152.

During the extension of left stylet 146 and/or right stylet 147 and during the procedure thereafter, tube extension 172 serves to support guide tube distalmost portions 154a against forces exerted against the stylets and guide cannulas 148 and 149 during the procedure. The bottom portion of tube extension 172 restricts distalmost portions 154a of the guide cannulas 148 and 149 from bending backwardly under these forces. Flared portions 173 of the tube extension 172 prevent the distalmost portions 154a from bending outwardly away from each other as the flared portions serve to cradle distal extremities 154a when distalmost portions 154a are in their bent or articulated positions. By so hindering movement of distalmost portions 154a from their known positions, catheter 21 permits more accurate placement of distal tips 227 of needle electrodes 226 during an electrosurgical procedure.

The unique placement of left and right guide cannulas 148 and 149 below the viewing face of the optical element permits greater visibility during the procedure because the distalmost portions 154a of guide tubes 152 do not generally obstruct the viewing region of the endoscope. As illustrated in FIGS. 1 and 8, viewing through endoscope 26 is particularly enhanced when the optical element of the endoscope is provided with a viewing face 28 which faces away from guide cannulas 148 and 149. The placement of distalmost portions 154a below the viewing face 28 permits the operating physician to view the bending of guide cannulas 148 and 149 and to easily observe the operating procedure performed by one or both of the needle electrodes 226 extending from the guide cannulas 148 and 149.

One or both needle electrodes 226 can be used during the electrosurgical procedure to perform single and/or dual coagulation. If only one needle electrode is extended, a conventional grounding element or pad must be placed against the patient to permit return of the radio frequency energy being supplied through the extended needle electrode 226. When both needle electrodes 226 are extended, monopolar coagulation can be performed by supplying radio frequency energy to either of the extended electrodes and utilizing the external pad as a ground return. Alternatively, bipolar coagulation can be performed by using one needle electrode as an energy supply electrode and the other needle electrode as a return or grounding electrode. As such, electrosurgical catheter 21 can be used for localized cutting, coagulation and dissection of tissue and is ideal for developing both small and large coagulative areas. First and second thermocouples 241 and 242 permit monitoring of the temperature in the tissue surrounding the targeted area of each needle electrode 226. Radio frequency generator and controller 367 is capable of providing both monopolar and bipolar radio frequency output at relatively low power of up to 50 watts.

Should left and right guide cannulas 148 and 149 need to be straightened partially or totally during the procedure, the relatively rigid push/pull ribbon or other actuation element carried within the guide cannulas 148 and 149 permits compressive forces to be exerted axially on the guide cannulas to straighten or extend their distalmost portions 154a.

Once the electrosurgical procedure has been completed inside of the body, finger lever 258 is moved away from opening 368 in the handle 23 so as to cause the extended stylets 146 and/or 147 to retract fully within respective guide cannulas 148 and 149. During this retraction stroke of actuation assemblies 251 and 252, stop 291 limits the pivoting of the engaged hood 281 about pin 286 thus causing the hood to return to its loaded position in which flexible stop 316 is in locked engagement with limit wall 327. The disengagement of plunger 331 with cross member 346 causes spring 341 to urge the plunger away from limit wall 327 thus permitting the flexible stop 316 to extend into first cutout 326. Lever 191 is moved to its distalmost position, shown in solid lines in FIG. 1, so that distalmost portions 154a of the guide tubes 152 are generally straightened as illustrated in FIGS. 1 and 8. The operating physician can now withdraw tube 36 from the urethra.

Sheath 22 and endoscope 26, once removed from handle 23, can be easily sterilized for reuse. In following procedures, another conventional rod lens endoscope such as one of endoscopes 26, 381, 421 or 436 can be easily utilized. In addition, a handle 23 can be selected in which needle electrodes 226 and actuation assemblies 251 and 252 have been sized so that the needle electrodes 226 extend from distal extremities 154a of guide tubes 152 a second and different predetermined distance within the previously described extension range. It should also be appreciated that a handle 23 can be provided in which the left and right needle electrodes 26 extend different distances from their respective guide tubes 152. For example, the left needle electrode 226 could extend from its guide tube 152 a distance less than the distance which the right needle electrode 226 extends from its guide tube.

Catheter 21 can also be used for performing a transurethral needle ablation procedure such as that described in copending U.S. patent application Ser. No. 08/191,258 filed Feb. 2, 1994.

In view of the foregoing, it can be seen that a new and improved electrosurgical catheter has been provided which can be adapted for use with a plurality of conventional rod lens endoscopes. The catheter includes a reusable sheath and at least one needle electrode which can be advanced sidewise of the longitudinal axis of the catheter at a selected angle ranging from 0 to 90°. A second needle electrode can be provided which can be selectively advanced or not advanced with the first needle electrode. The catheter permits a generally unobstructed view of the needle electrodes advancing toward the target region in the body and includes guide cannulas provided with T-shaped slots for providing a relatively smooth bend in the guide cannulas. A substantially rigid pull/push member is provided in the guide cannulas for bending and straightening of the guide cannulas.

What is claimed is:

1. A transurethral needle ablation device for use by a human hand to treat the prostate of a human male using radio frequency energy from a radio frequency power source, the human male having a bladder with a base, a prostate and a penis with a urethra therein formed by a urethral wall extending from the base of the bladder through the prostate and the penis along a longitudinal axis with the prostate having tissue surrounding the urethral wall near the base of the bladder, comprising an elongate probe member having proximal and distal extremities and having a passageway extending from the proximal extremity to the distal extremity, a stylet slidably mounted in the passageway of the elongate probe member and having proximal and distal extremities, the stylet having a radio frequency conductive electrode and a layer of insulating material longitudinally disposed on the radio frequency conductive electrode for slidable movement thereon, handle means adapted to be grasped by the human hand coupled to the proximal extremity of the elongate probe member, connector means connected to the radio frequency conductive electrode and adapted to be coupled to the radio frequency power source for supplying radio frequency energy to the radio frequency conductive electrode, a finger actuatable element mounted on the handle means and adapted to be grasped by a finger of the hand grasping the handle means, the finger actuatable element being movable in one direction from a first position to a second position, means connecting the finger actuatable element to the stylet for initially maintaining the radio frequency conductive electrode and the insulating sleeve disposed thereon substantially stationary relative to one another while introducing the radio frequency conductive electrode and the insulating sleeve disposed thereon in unison into the tissue of the prostate when the finger actuatable element is moved in the one direction from the first position toward the second position and thereafter for causing at least a portion of the radio frequency conductive electrode to be exposed free of the layer of said insulating material in the tissue of the prostate as the finger actuatable element is moved further in the one direction toward the second position.

2. A device as in claim 1 wherein the means connecting the finger actuatable element to the stylet for causing at least a portion of the radio frequency conductive electrode to be exposed free of the layer of said insulating material in the tissue of the prostate as the finger actuatable element is moved further in the one direction toward the second position includes means connecting the finger actuatable element to the radio frequency conductive electrode and the layer of insulating material of the stylet for causing relative movement between the radio frequency conductive electrode and the layer of insulating material.

3. A device as in claim 1 for use with a first endoscope having a first length and a first distal portion and a second endoscope having a second length different than the first length and a second distal portion wherein the elongate probe member is provided with an opening in the distal extremity in communication with the passageway, an adapter assembly carried by the proximal extremity of the elongate probe member for securing the first endoscope to the elongate probe member so that the first distal portion of the first endoscope extends in the passageway to a point adjacent the opening for viewing forwardly of the elongate probe member and for alternatively securing the second endoscope to the elongate probe member so that the second distal portion of the second endoscope extends in the passageway to a point adjacent the opening for viewing forwardly of the elongate probe member.

4. A device as in claim 1 wherein the means connecting the finger actuatable element to the stylet for causing at least a portion of the radio frequency conductive electrode to be exposed free of the layer of said insulating material in the tissue of the prostate as the finger actuatable element is further moved in the one direction toward the second position includes means connecting the finger actuatable element to the radio frequency conductive electrode and the layer of insulating material of the stylet for causing the layer of insulating material to retract relative to the radio frequency conductive electrode.

5. A device as in claim 4 wherein the means connecting the finger actuatable element to the radio frequency conductive electrode and the layer of insulating material of the stylet for causing the layer of insulating material to retract relative to the radio frequency conductive electrode includes means connecting the finger actuatable element to the radio frequency conductive electrode and the layer of insulating material of the stylet for causing the layer of insulating material to retract automatically relative to the radio frequency conductive electrode.

6. A device for medical treatment of tissue at a treatment site through a natural body opening comprising an elongate probe member having proximal and distal extremities and having a longitudinal axis, the elongate probe member having a sidewall with a passageway therein extending along the longitudinal axis, a radio frequency electrode disposed in the passageway, an insulating sleeve disposed on the radio frequency electrode for slidable longitudinal movement thereon, a handle coupled to the proximal extremity of the elongate probe member, finger operable means carried by the handle and connected to the radio frequency electrode and to the insulating sleeve for causing movement of the radio frequency electrode and the sleeve in the passageway and guide means carried by the elongate probe member and cooperatively coupled into the passageway for directing the radio frequency electrode and the insulating sleeve through a curved path extending at an angle to the longitudinal axis toward the tissue at the treatment site, the finger operable means including means for causing the radio frequency electrode and the insulating sleeve to extend from the elongate probe member in unison to a predetermined distance from the elongate probe member into the tissue at the treatment site and thereafter for causing the insulating sleeve to automatically retract relative to the elongate probe member when the radio frequency electrode is extended beyond the predetermined distance.

7. A device as in claim 6 wherein the means for directing the radio frequency electrode and the insulating sleeve through a curved path includes a guide cannula mounted in the passageway of the elongate probe member and having proximal and distal extremities and a lumen extending therethrough from the proximal extremity to the distal extremity, the radio frequency electrode and the insulating sleeve being disposed in the lumen, and means carried by the handle for causing bending of the distal extremity of the guide cannula.

8. An electrosurgical device for medical treatment of tissue at a treatment site beyond a wall defining a natural body cavity accessible from outside the body by a natural body opening comprising an elongate probe member having proximal and distal extremities and a sidewall for forming a passage extending from the proximal extremity to the distal extremity, the elongate probe member being provided with an opening in the distal extremity in communication with the passageway and an elongate cutout in the sidewall adjacent the opening, the elongate probe member being formed with an elongate extension projecting alongside the cutout beyond the opening, a guide cannula mounted in the passage of the elongate probe member and having proximal and distal extremities and a lumen extending therethrough from the proximal extremity to the distal extremity, the distal extremity of the guide cannula being provided with a cylindrical wall having at least a portion thereof containing a plurality of longitudinally spaced-apart circumferentially-extending slots subtending less than 360° formed therein to provide a flexible portion, a handle coupled to the proximal extremity of the guide cannula, means carried by the handle for causing bending of the distal extremity of the guide cannula at the flexible portion towards the cutout whereby the distal extremity of the guide cannula is movable to a bent position, a radio frequency electrode disposed in the lumen, an insulating sleeve extending around the radio frequency electrode but exposing a distal portion of the radio frequency electrode, means carried by the handle and secured to the radio frequency electrode and the insulating sleeve for advancing the radio frequency electrode and the insulating sleeve from the guide cannula through the wall to the treatment site and means for restricting backwards motion of the distal extremity of the guide cannula away from said cutout as the radio frequency electrode penetrates the wall, said means for restricting backwards motion of the distal extremity of the guide cannula including said elongate extension whereby rear support is provided to the distal extremity of the guide cannula when in its bent position against the force exerted by the radio frequency electrode on the guide cannula as the radio frequency electrode penetrates the wall.

9. A device as in claim 8 wherein the means for advancing the radio frequency electrode and the insulating sleeve includes means for causing relative movement between the radio frequency electrode and the insulating sleeve.

10. A device as in claim 8 wherein the insulating sleeve has a distal extremity and further comprising first and second temperature sensing means carried by the distal extremity of the insulating sleeve in longitudinally spaced-apart positions.

11. A device as in claim 8 wherein the means for causing bending of the distal extremity of the guide cannula permits the distal extremity of the guide cannula to be bent at a plurality of preselected angles ranging from 0° to 90°.

12. A device as in claim 1 wherein the handle includes scissor-type grip.

13. A device as in claim 8 wherein the slots are T-shaped.

14. A device as in claim 8 wherein the slots are circumferentially aligned to provide a backbone extending longitudinally of the flexible portion so as to permit bending in only a single direction.

15. A device as in claim 14 wherein the backbone tapers as it extends distally through the flexible portion.

16. A device as in claim 8 further comprising a guide cannula of the same type as the first named guide cannula mounted in the passage of the elongate probe member alongside the first named guide cannula and an additional radio frequency electrode and insulating sleeve of the same type as the first named radio frequency electrode and insulating sleeve disposed in the lumen of the additional guide cannula and wherein the means for advancing is secured to the additional radio frequency electrode and the additional insulating sleeve and wherein the means for causing bending of the distal extremity of the first named guide cannula towards the cutout causes bending of the distal extremity of the additional guide cannula towards the cutout.

17. A device as in claim 16 wherein the means for advancing the radio frequency electrodes and the insulating sleeves causes the first named radio frequency electrode and insulating sleeve to be advanced singly or together with the additional radio frequency electrode and insulating sleeve.

18. A device as in claim 16 wherein the extension of the elongate probe member includes spaced apart first and second side portions which flare outwardly from each other for providing lateral support to the radio frequency electrodes when they extend outwardly from each other through the cutout.

19. A device as in claim 16 adapted for use with an endoscope having an elongate optical element with a distal viewing face wherein the elongate probe member is cross-sectionally sized to permit the optical element to extend adjacent the guide cannulas so that the distal extremities of the guide cannulas extend in front of the viewing face of the optical element as the guide cannulas bend towards the cutout.

20. A device as in claim 8 for use with first or second endoscopes for introduction through the natural body opening into a canal defined by a wall, the first endoscope having a first length and a first proximal portion with a first coupling extension and a first optical element extending to a first distal portion and the second endoscope having a second length different than the first length and a second proximal portion with a second coupling extension and a second optical element extending to a second distal portion, wherein the elongate probe member has a longitudinal axis, coupling means carried by the proximal extremity of the elongate probe member and adapted to alternatively secure the first and second endoscopes to the elongate probe member, the coupling means including first adapter,means for engaging the first coupling extension of the first endoscope and removable second adapter means for engaging the second coupling extension of the second endoscope, the first adapter means being longitudinally sized so that the first distal portion of the first endoscope extends in the passageway to a point adjacent the opening for viewing forwardly of the elongate probe member and having first cooperative means for mating with the first coupling extension to restrict rotation of the first endoscope about the longitudinal axis and the second adapter means being longitudinally sized so that the second distal portion of the second endoscope extends in the passageway to a point adjacent the opening for viewing forwardly of the elongate probe member and having second cooperative means for mating with the second coupling extension to restrict rotation of the second endoscope about the longitudinal axis.

21. A device as in claim 20 for use with a third endoscope having a third length different from the first and second lengths and a third proximal portion with a third coupling extension and a third optical element extending to a third distal portion wherein the coupling means includes removable third adaptor means for engaging the third coupling extension of the third endoscope, the third adaptor means being longitudinally sized so that the third distal portion of the third endoscope extends in the passageway to a point adjacent the opening for viewing forwardly of the elongate probe member and having third cooperative means for mating with the third coupling extension to restrict rotation of the third endoscope about the longitudinal axis.

22. A device as in claim 20 further comprising a substantially annular element made from an elastomeric material disposed in the passageway for circumferentially engaging the respective optical element and means for compressing the annular element so that it extends inwardly against the optical element to secure the respective optical element in the elongate probe member.

23. A sheath as in claim 22 wherein the annular element is an O-ring.

24. A sheath as in claim 22 wherein the proximal extremity of the elongate member is provided with an annular recess for receiving the annular element and wherein the means for compressing the annular element includes a washer-like element disposed in the annular recess in juxtaposition to the annular element and means for exerting a compressive axial force against the washer-like element.

25. A device as in claim 24 wherein the means for exerting a compressive axial force against the washer-like element includes a yolk member extending transversely across the passageway adjacent to the washer-like element and being provided with a bore in alignment with the passageway for receiving the respective optical element, the yolk member having a first end pivotally coupled to the proximal extremity of the elongate probe member and an opposite second end and means connected to the second end for causing the yolk member to pivot about the first end whereby the yolk member exerts a compressive force on the washer-like element when it is pivoted toward the washer-like element.

26. A sheath as in claim 25 further comprising a ring member rotatably carried about the proximal extremity of the elongate member and means coupling the ring member to the second end of the yolk member so that rotation of the ring member in a first direction about the longitudinal axis pivots the yolk member toward the washer-like element and rotation of the ring member in an opposite second direction pivots the yolk member away from the washer-like element.

27. A device as in claim 8 wherein the means for causing bending of the distal extremity of the guide cannula includes means for straightening the distal extremity of the guide cannula.

28. A device as in claim 27 wherein the means for straightening the distal extremity of the guide cannula includes an elongate actuation element connected to the guide cannula distal of the flexible portion, the elongate actuation element having a proximal end portion and having a cross-sectional shape which inhibits buckling of the elongate actuation element when a compressive force is exerted axially on the proximal end portion of the elongate actuation element.

29. A device as in claim 28 wherein the elongate actuation element is in the form of an elongate strip.

30. A device as in claim 28 wherein the elongate actuation element is in the form of a tubular member.

31. A device as in claim 20 wherein the tubular member extends longitudinally between the guide cannula and the insulating sleeve.

32. A device as in claim 31 wherein the tubular member is provided with a cylindrical wall having at least a portion thereof containing a plurality of longitudinally spaced-apart circumferentially-extending slots subtending less than 360° formed therein to provide a flexible portion in the tubular member.

33. A device as in claim 31 wherein the tubular member is provided with a cylindrical wall having an elongate cutout formed therein to provide a flexible portion in the tubular member.

* * * * *